(12) United States Patent
Takaishi

(10) Patent No.: US 10,842,689 B2
(45) Date of Patent: Nov. 24, 2020

(54) STRETCH STRUCTURE FOR ABSORBENT ARTICLE, AND UNDERPANTS-TYPE DISPOSABLE DIAPER USING SAME

(71) Applicant: Daio Paper Corporation, Ehime (JP)

(72) Inventor: Mina Takaishi, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 325 days.

(21) Appl. No.: 15/546,990

(22) PCT Filed: Jan. 29, 2016

(86) PCT No.: PCT/JP2016/052804
§ 371 (c)(1),
(2) Date: Jul. 27, 2017

(87) PCT Pub. No.: WO2016/121974
PCT Pub. Date: Aug. 4, 2016

(65) Prior Publication Data
US 2018/0028371 A1    Feb. 1, 2018

(30) Foreign Application Priority Data

Jan. 30, 2015  (JP) ................. 2015-017498

(51) Int. Cl.
| | | |
|---|---|---|
| A61F 13/515 | (2006.01) | |
| A61F 13/496 | (2006.01) | |
| A61F 13/49 | (2006.01) | |
| A61F 13/514 | (2006.01) | |

(52) U.S. Cl.
CPC ............ *A61F 13/515* (2013.01); *A61F 13/49* (2013.01); *A61F 13/496* (2013.01);
(Continued)

(58) Field of Classification Search
CPC .............. A61F 13/515; A61F 13/49011; A61F 13/496; A61F 13/53; A61F 13/49009;
(Continued)

(56) References Cited

U.S. PATENT DOCUMENTS

| | | | |
|---|---|---|---|
| 6,572,595 B1 | 6/2003 | Klemp et al. | |
| 2010/0168705 A1* | 7/2010 | Stabelfeldt | ........ A61F 13/15593 604/367 |

(Continued)

FOREIGN PATENT DOCUMENTS

| | | |
|---|---|---|
| CN | 103717188 | 4/2014 |
| EP | 0547497 | 6/1993 |

(Continued)

*Primary Examiner* — Ophelia A Hawthorne
*Assistant Examiner* — Heather K Barnwell
(74) *Attorney, Agent, or Firm* — Muncy, Geissler, Olds & Lowe, P.C.

(57) ABSTRACT

A stretchable structure of an absorbent article includes a stretchable region and a non-stretchable region. A laminate of a first sheet layer, second sheet layer, and elastic film between the first and second sheet layers extends over the stretchable and non-stretchable regions. The first and second sheet layers are bonded to each other at a large number of dot-like joints via through holes formed in the elastic film stretched along the surfaces of the first and second sheet layers in a stretchable direction. The dot-like joints are arrayed at intervals in the stretchable direction and a direction perpendicular to the stretchable direction. An end of the stretchable region adjacent to the non-stretchable region is a buffer stretchable section. The area rate of dot-like joints in the buffer stretchable section is larger than the area rate of dot-like joints in the main section not including the buffer stretchable section.

5 Claims, 14 Drawing Sheets

(52) U.S. Cl.
CPC ...... *A61F 13/49019* (2013.01); *A61F 13/514* (2013.01); *A61F 13/51464* (2013.01); *A61F 13/51474* (2013.01); *A61F 13/51476* (2013.01); *A61F 13/51478* (2013.01)

(58) Field of Classification Search
CPC ............ A61F 13/4901; A61F 13/49012; A61F 13/49013; A61F 13/49014; A61F 13/49015; A61F 13/51464; A61F 13/51476
See application file for complete search history.

(56) References Cited

U.S. PATENT DOCUMENTS

| | | | |
|---|---|---|---|
| 2010/0215923 A1 | 8/2010 | Frost | |
| 2010/0312211 A1* | 12/2010 | Bond | A61F 13/5376 604/378 |
| 2011/0319853 A1 | 12/2011 | Yamashita et al. | |
| 2014/0093703 A1* | 4/2014 | Hanschen | B32B 5/142 428/175 |
| 2014/0257219 A1* | 9/2014 | Neton | A61F 13/51401 604/365 |

FOREIGN PATENT DOCUMENTS

| | | | | |
|---|---|---|---|---|
| EP | 3202383 A1 | 8/2017 | | |
| JP | 10-029259 A | 2/1998 | | |
| JP | 2004532758 | 10/2004 | | |
| JP | 2006-198132 | 8/2006 | | |
| JP | 2008-260131 | 10/2008 | | |
| JP | 4508885 B2 | 7/2010 | | |
| JP | 2010195044 A | 9/2010 | | |
| JP | 2010195044 A | 9/2010 | | |
| JP | 2010200974 A | 9/2010 | | |
| JP | 2010200974 A | 9/2010 | | |
| JP | 4934835 B2 | 5/2012 | | |
| JP | 2014150917 A | 8/2014 | | |
| JP | 2014150917 A | 8/2014 | | |
| JP | 2016140477 | 8/2016 | | |
| JP | 2016-185265 A | 10/2016 | | |
| JP | 6383712 B2 | 8/2018 | | |
| WO | WO03/000165 A1 | 1/2003 | | |
| WO | WO-03000165 A1 * | 1/2003 | ............... | A47L 1/15 |
| WO | WO2008/126708 A1 | 10/2008 | | |
| WO | WO2011/048512 | 4/2011 | | |
| WO | WO-2012/038571 A2 | 3/2012 | | |

* cited by examiner

FIG.9
(a)
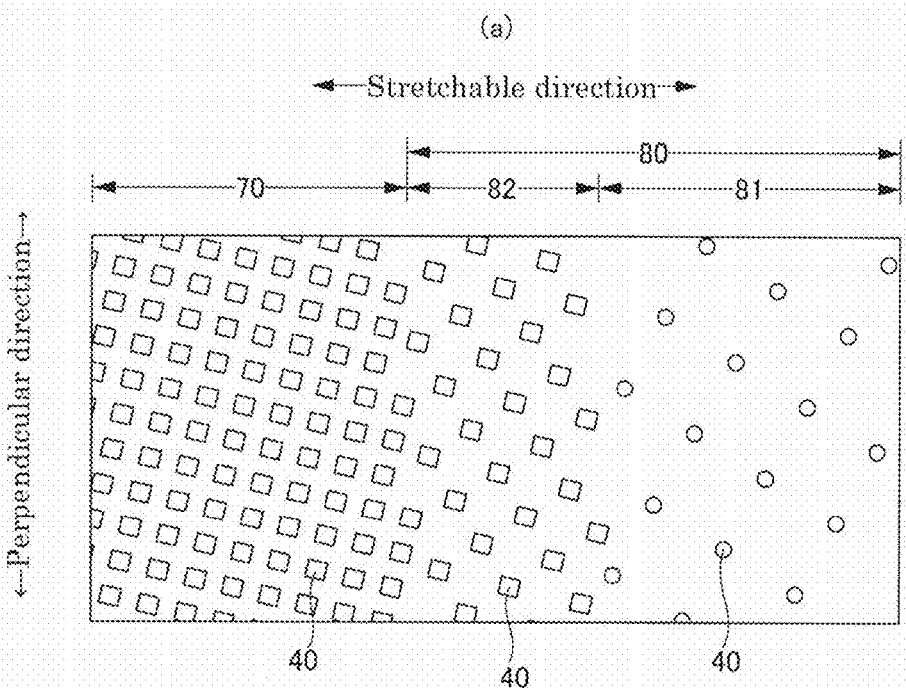
(b)
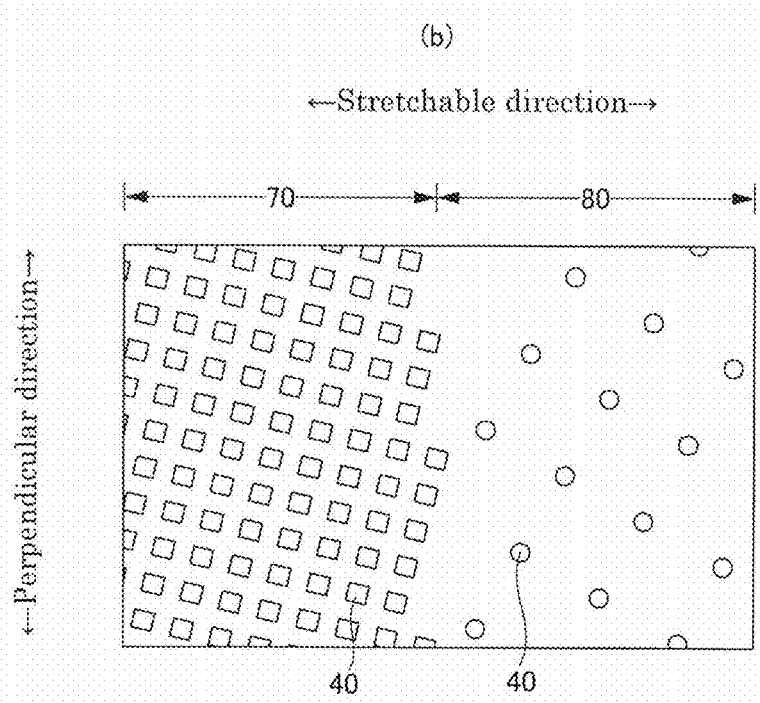

STRETCH STRUCTURE FOR ABSORBENT ARTICLE, AND UNDERPANTS-TYPE DISPOSABLE DIAPER USING SAME

TECHNICAL FIELD

The present invention relates to a stretchable structure of an absorbent article including sheet layers and an elastic film disposed therebetween.

BACKGROUND ART

In absorbent articles, leg portions and a waist portion generally have elasticity for better fitness to the surfaces of the bodies. In order to impart elasticity to these portions, a typical approach has been widely adopted which involves a large number of fixing elongated elastically stretchable members, such as rubber threads, in a state stretched in the longitudinal direction. Another approach has been proposed which involves fixing an elastic film in a state stretched in the elastically stretching direction (refer to, for example, Patent Literature 1), to produce absorbent articles having excellent fitness to the surfaces of the bodies.

Such a stretchable structure including a laminate of the sheet layers and the elastic film disposed between the sheet layers (hereinafter also referred to as elastic-film stretchable structure) has the following configuration: The stretchable structure has a stretchable region composed of a laminate of a first sheet layer, a second sheet layer, and an elastic film between the first sheet layer and the second sheet layer. The elastic film is stretched in a stretchable direction along the surfaces of the first and second sheet layers, and the first sheet layer and the second sheet layer are bonded to each other at a large number of dot-like joints via through holes formed in the elastic film. The dot-like joints are arrayed at intervals in the stretchable direction and in a direction perpendicular to the stretchable direction. While the elastic-film stretchable structure is in the natural-length state, the elastic film between the dot-like joints is being contracted and thus the intervals between the dot-like joints are being decreased, forming contracted wrinkles, extending through the intervals between the dot-like joints in a direction intersecting with the stretchable direction, of the first sheet layer and the second sheet layer. In contrast, while the elastic-film stretchable structure is in a stretched state, the elastic film between the dot-like joints is being stretched, and the contracted wrinkles, extending through the intervals between the dot-like joints, of the first sheet layer and the second sheet layer, are being stretched. The first and second sheet layers can be thereby elastically stretched to a completely stretched state. Such an elastic-film stretchable structure is superior in surface fitness and excellent in softness because the first and second sheet layers are not bonded to the elastic film and the first sheet layer and the second sheet layer are bonded to each other at significantly reduced joints. In addition, the through holes formed in the elastic film advantageously contributes to air permeability of the elastic-film stretchable structure.

In order to simplify the manufacture of absorbent articles having a stretchable region only at a given position, an approach has been adopted which involves fixing elastically stretchable members in a large area including the stretchable region requiring elasticity, and performing a process to reduce or eliminate the contraction force of the elastically stretchable members to form a non-stretchable region requiring no elasticity (hereinafter also referred to as eliminating elasticity). For example, to impart elasticity in the width direction to the torso portions of an underpants-type disposable diaper, a typical approach has been widely adopted which involves fixing elongated elastically stretchable members over the entire width direction, and cutting some of elastically stretchable members overlapping with an absorber disposed at a middle of the width direction into small fractions to eliminate the elasticity of the elastically stretchable members.

Such an approach to eliminate the elasticity of the stretchable structure including rubber threads by cutting the rubber threads, however, cannot be adopted to the elastic-film stretchable structure. Through examination of approaches to eliminate the elasticity of the elastic-film stretchable structure, the inventor of the present invention has found that the elasticity can be substantially eliminated by increasing the area rate (per unit area) of the dot-like joints above a certain level. The approach found by the inventor can substantially eliminate the elasticity while maintaining the continuity of the elastic film in the stretchable region and the non-stretchable region, and can produce an absorbent article having a good appearance.

CITATION LIST

Patent Literature

Patent Literature 1: Japanese Unexamined Patent Application Publication (Translation of PCT Application) No. 2004-532758

SUMMARY OF INVENTION

Technical Problem

If the area rate of the dot-like joints exceeds a certain level in a non-stretchable region, the number of the through holes formed in the elastic film increases at an end of the non-stretchable region adjacent to the stretchable region. The increased through holes work as a highly breakable perforation lines running along a boundary between the stretchable region and the non-stretchable region. Unfortunately, the elastic film may be ruptured along the boundary between the stretchable region and the non-stretchable region by tension applied during the manufacture or the use of the absorbent article.

A main object of the present invention is to provide a stretchable structure of an absorbent article that includes a laminate of sheet layers and a single elastic film between the sheet layers and has both of a stretchable region and a non-stretchable region in the laminate. The stretchable structure can prevent a rupture of the elastic film along a boundary between the stretchable region and the non-stretchable region.

Solution to Problem

The present invention, which solves the disadvantages described above, has the following configuration.

<The Invention of Claim 1>

A stretchable structure of an absorbent article comprising:
a stretchable region stretchable in at least one direction; and
a non-stretchable region continuing from the stretchable region, wherein
a laminate comprising a first sheet layer, a second sheet layer, and an elastic film disposed between the first sheet layer and the second sheet layer extends over the stretchable region and the non-stretchable region, the first sheet layer and the second sheet layer are bonded to each other at a large number of dot-like joints via through holes formed in the elastic film stretched along the surfaces of the first sheet layer and the second sheet layer in a stretchable direction, the dot-like joints being arrayed at intervals in the stretchable direction and a direction perpendicular to the stretchable direction, the area rate of the dot-like joints in the non-stretchable region is larger than the area rate of the dot-like joints in the stretchable region, and the non-stretchable region has an elongation at elastic limit of 130% or less in the stretchable direction, the area rate of the dot-like joints in the stretchable region is smaller than the area rate of the dot-like joints in the non-stretchable region, and the stretchable region has an elongation at elastic limit of 200% or larger, an end of the stretchable region adjacent to the non-stretchable region is a buffer stretchable section, the area rate of the dot-like joints in the buffer stretchable section being larger than the area rate of the dot-like joints in a main stretchable section not including the buffer stretchable section.

<Operational Advantage>

Basically, in the elastic-film stretchable structure according to an embodiment of the present invention, portions, contracted by the elastic film, of the first and second sheet layers decrease and the elongation at elastic limit is thereby likely to be reduced with an increase in the area rate of the dot-like joints. With an increase in the area rate of the dot-like joints, the area rate of the through holes formed in the elastic film increases, and the proportion of portions of the elastic film continuing in the stretchable direction decreases in the direction perpendicular to the stretchable direction. The contraction force generated in the stretched state is thereby likely to be reduced and the risk of rupture of the elastic film increases. The term "elongation at elastic limit" used herein indicates the proportion of the lengths at elastic limit (in other words, in the completely stretched states of the first and second sheet layers) relative to the natural-length (100%) in percentage. The term "area rate" indicates the proportion of the target portions per unit area, i.e., the total area of the target portions (for example, dot-like joints and openings of the through holes) divided by the area of the target region (for example, stretchable region, non-stretchable region, main stretchable section, or buffer stretchable section) in percentage. In particular, the term "the area rate of dot-like joints" indicates the area rate of dot-like joints at elongation at elastic limit in the stretchable direction.

In view of the characteristics described above, the following variations are assumed to be caused in the stretchable structure of the present invention including the buffer stretchable section (corresponding to the end of the stretchable region disposed adjacent to the non-stretchable region and having a larger area rate of the dot-like joints than that of the main stretchable section corresponding to a remaining portion of the stretchable region other than the buffer stretchable section), when the stretchable structure is stretched.

In the case where the buffer stretchable sections and the main stretchable sections are stretched from the natural-length state by gradually increasing stress, there are the first phase and the second phase. In the first phase, while both of the buffer stretchable sections and the main stretchable sections are stretched, the buffer stretchable sections are stretched to the elastic limit into a completely stretched state earlier than the main stretchable sections and the main stretchable sections are in an incompletely stretched state. The main stretchable sections go through the first phase, and then the second phase where the main stretchable sections are stretched to the elastic limit into a completely stretched state. In the first phase, the buffer stretchable sections having at a low elongation at elastic limit are stretched; therefore, a small tension is applied to a boundary between the buffer stretchable section and the non-stretchable region of the elastic film. A rupture of the elastic film at the boundary between the buffer stretchable section and the non-stretchable region is thereby prevented. In the second phase, tension corresponding to the elongation of the main stretchable section is applied to the main stretchable section, the buffer stretchable section, and the non-stretchable region until the main stretchable section is in a completely stretched state; however, since the buffer stretchable section cannot be stretched any more after the first phase, tension applied to the non-stretchable region and the buffer stretchable section is entirely supported by the first sheet layer and the second sheet layer. As a result, the tension applied to the boundary between the buffer stretchable section and the non-stretchable region of the elastic film does not exceed the elongation at elastic limit in the first phase. The rupture of the elastic film along the boundary between the buffer stretchable section and the non-stretchable region is thereby prevented, as in the first phase.

To prevent the rupture of the elastic film or to prevent an inferior appearance after the rupture, a part of the elastic film at the end of the stretchable region adjacent to the non-stretchable region may be bonded to the first and second sheet layers with hot melt adhesive for reinforcement; however, the use of hot melt adhesive is not preferred because it impairs softness and air permeability of the hot-melted part. In contrast, the present invention can address the disadvantages by varying the area rate of dot-like joints in the elastic film to prevent the rupture of the elastic film. It should be noted that the present invention may involve the reinforcement with hot melt adhesive in combination with the variation in the area rate of the dot-like joints.

<The Invention of Claim 2>

The stretchable structure of the absorbent article according to claim 1, wherein the dot-like joints are formed by welding materials of the first sheet layer and the second sheet layer, and at least edges of the through holes formed in the elastic film are cured.

<Operational Advantage>

The dot-like joints may be formed by any process. In terms of high production throughput, heat sealing or ultrasonic sealing is preferred to form the array of the dot-like joints on the laminate of the first sheet layer, the second sheet layer, and the elastic film disposed between the first sheet layer and the second sheet layer, because such sealing can form through holes in the elastic film, and, at the same time, can bond the first sheet layer to the second sheet layer via the through holes. The sealing, however, is likely to cause thermal curing of the edges of the through holes. Cured edges of the through holes in the end of the non-stretchable region adjacent to the stretchable region is fragile, and are thus likely to cause a rupture of the elastic film along the boundary between the stretchable region and the non-stretchable region. The configuration of the present invention can appropriately address these disadvantages.

<The Invention of Claim 3>

The stretchable structure of the absorbent article according to claim 1, wherein
- each of the dot-like joints has an area of 0.14 to 3.5 mm$^2$,
- each of the through holes has an area that is 1 to 1.5 times the area of each of the dot-like joints,
- an area rate of the dot-like joints is 16 to 45% in the non-stretchable region,
- an area rate of the dot-like joints is 1.8 to 19.1% in the main stretchable section,
- an area rate of the dot-like joints is 8 to 22.5% in the buffer stretchable section.

<Operational Advantage>

The area of each dot-like joint and the area of an opening of each through hole may be appropriately determined, preferably within the range described above. The area of the opening of the through hole indicates the area of the opening of the through hole when the stretchable structure is in the natural-length state. If the through hole has different opening areas across the thickness, i.e., if the openings of the through hole are different in area in the front and back face of the elastic film, the area of the opening of the through hole indicates a maximum area.

<The Invention of Claim 4>

The stretchable structure of the absorbent article according to claim 1, wherein
the elastic film has a tensile strength of 8 to 25 N/35 mm in the stretchable direction, a tensile strength of 5 to 20 N/35 mm in a direction perpendicular to the stretchable direction, a tensile elongation of 450 to 1050% in the stretchable direction, and a tensile elongation of 450 to 1400% in the direction perpendicular to the stretchable direction.

<Operational Advantage>

Any elastic film may be used, and preferred is the elastic film having the characteristics described above. The tensile strength and the tensile elongation at break are measured at an initial chuck interval of 50 mm and a speed of testing of 300 mm/min with a tensile tester (for example, AOUT-GRAPHAGS-G100N available from SHIMADZU) in accordance with JIS K7127:1999 "Plastics—Determination of tensile properties", except that the test piece is a rectangle with a width of 35 mm and a length of 80 mm.

<The Invention of Claim 5>

The stretchable structure of the absorbent article according to claim 1, wherein
the elongation at elastic limit of each of the buffer stretchable section is smaller than a tensile elongation in the stretchable direction of the elastic film having a width equal to an interval between two adjacent through holes formed in the elastic film and arrayed in the direction perpendicular to the stretchable direction in the non-stretchable region.

<Operational Advantage>

Since the elongation of elastic limit of the buffer stretchable section is smaller than the tensile elongation of the part of the elastic film susceptible to rupture, the rupture of the elastic film along the boundary between the stretchable region and the non-stretchable region can be certainly prevented.

An underpants-type disposable diaper comprising:
- an outer member comprising a front body and a back body; and
- an inner member comprising an absorber, the inner member being fixed to the internal face of the outer member, wherein
- two side edges of the front body of the outer member are respectively bonded to two side edges of the back body of the outer member to define side seal portions, and an annular torso, a waist opening, and paired leg openings are thereby formed,
- the outer member has the stretchable structure of the absorbent article according to claim 1 such that the stretchable structure is stretchable along a width direction, and
- the non-stretchable region is a part of the outer member overlapping with the absorber, the stretchable regions continue from two sides of the non-stretchable region in the width direction.

<Operational Advantage>

For simple manufacturing of an underpants-type disposable diaper, it is desirable to dispose the elastic film over non-elastic portion of the outer member overlapping with the absorber. The present invention is appropriately adopted to eliminate elasticity in the non-elastic portion.

Advantageous Effect

According to the present invention described above, the stretchable structure of an absorbent article, in which a laminate of sheet layers and a single elastic film disposed therebetween extends over the stretchable region and the non-stretchable region, can advantageously prevent the rupture of the elastic film along the boundary between the stretchable region and the non-stretchable region.

BRIEF DESCRIPTION OF DRAWINGS

FIG. 9(a) is a schematic plan view of the main portion of the outer member in a completely stretched state in one embodiment; FIG. 9(b) is a schematic plan view of the main portion of the outer member in a completely stretched state in another embodiment.

DESCRIPTION OF EMBODIMENTS

Figure 1:
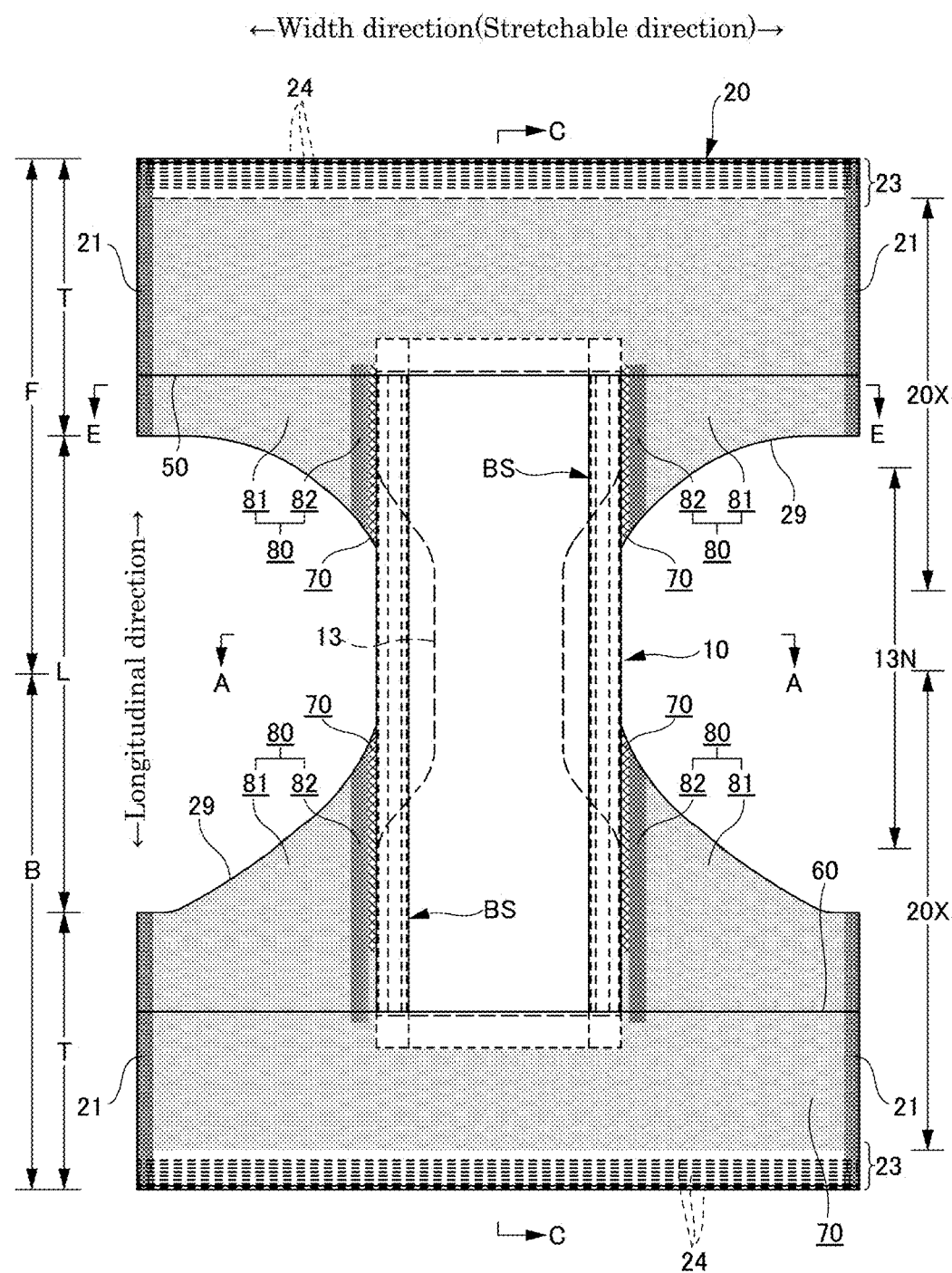
FIG. 1 is a plan view illustrating the internal surface side of an underpants-type disposable diaper in a completely stretched state.

Embodiments of the present invention will now be described in detail with reference to the accompanying drawings. The dots in cross-sectional views represent bonding means, for example, hot-melt adhesive.

FIGS. 1 to 7 illustrate an underpants-type disposable diaper. The underpants-type disposable diaper (hereinafter simply referred to as diaper) has an outer member 20 composed of a front body F and a back body B, and an inner member 10 that is fixed in a unified manner to the internal face of the outer member 20. The inner member 10 has a liquid-permeable front face sheet 11, a liquid-impermeable back face sheet 12, and an absorber 13 between the front face sheet 11 and the back face sheet 12. The manufacture of the underpants-type disposable diaper involves bonding the back face of the inner member 10 to the internal (upper) face of the outer member 20 with bonding means, for example, hot-melt adhesive (shaded area 10B in FIG. 7); folding the inner member 10 and the outer member 20 at an intermediate portion in the longitudinal (front-back) direction, i.e., along the dividing line extending between the front body F and the back body B; and bonding opposite side edges into side seal portions 21 by thermal welding or with hot-melt adhesive to define a waist opening and a pair of leg openings.

<Exemplary Structure of Inner Member>

Figure 4:
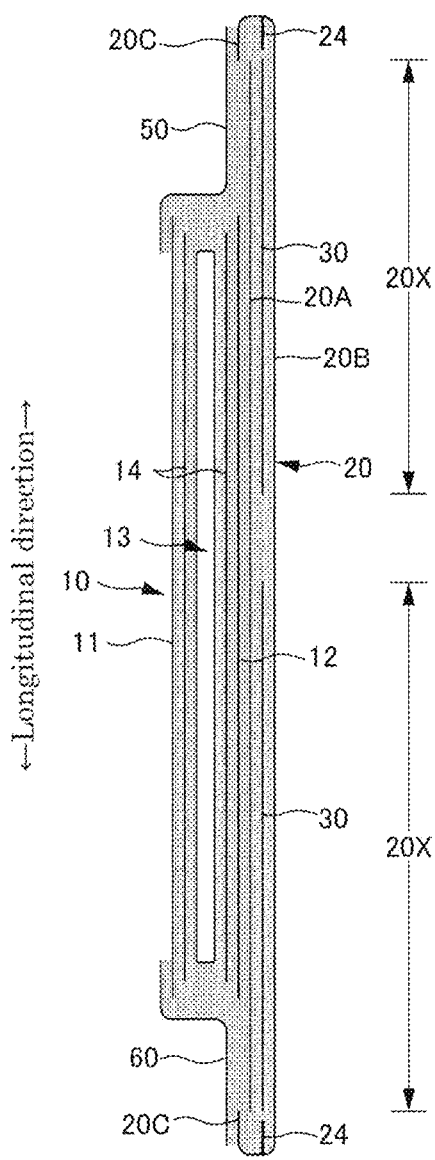
FIG. 4 is a cross-sectional view taken along the line C-C in FIG. 1.
Figure 5:
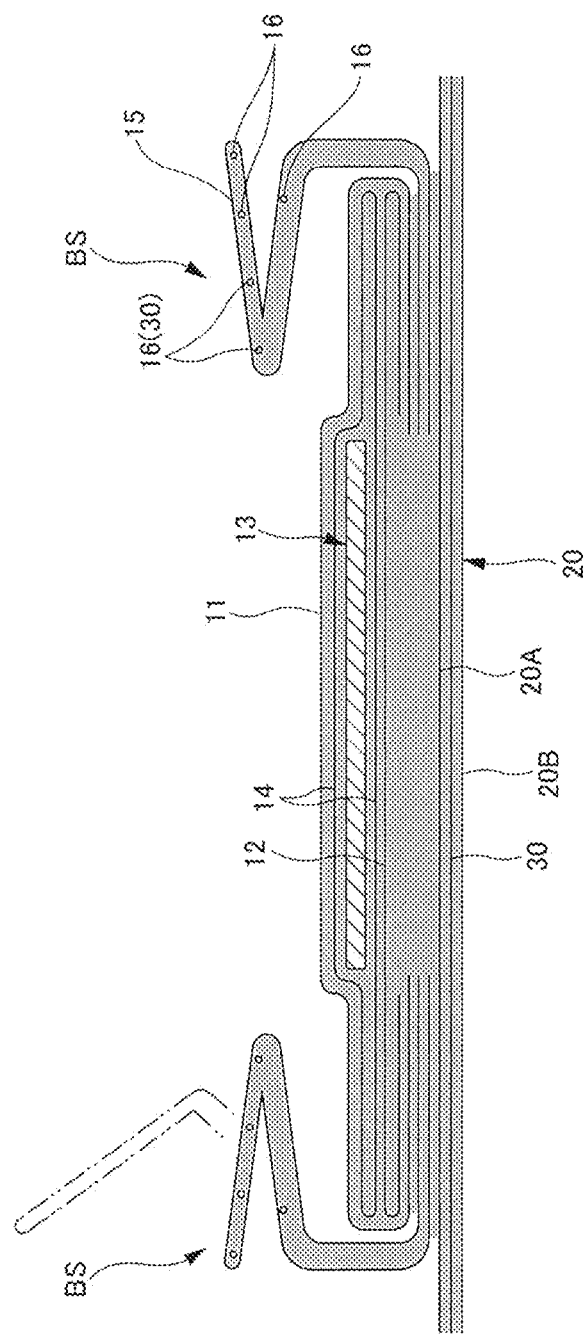
FIG. 5 is a cross-sectional view taken along the line A-A in FIG. 1.
Figure 6:
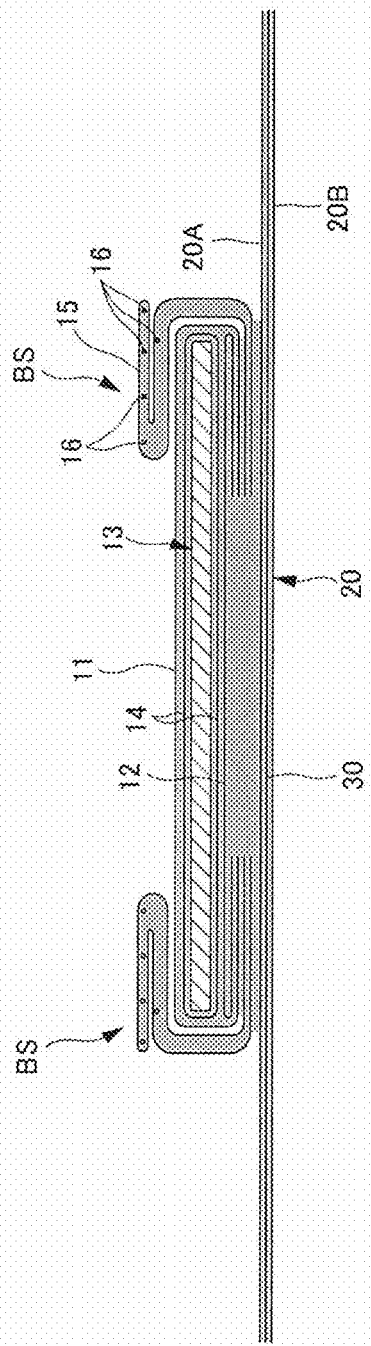
FIG. 6 is a cross-sectional view taken along the line E-E of FIG. 1.
Figure 7:
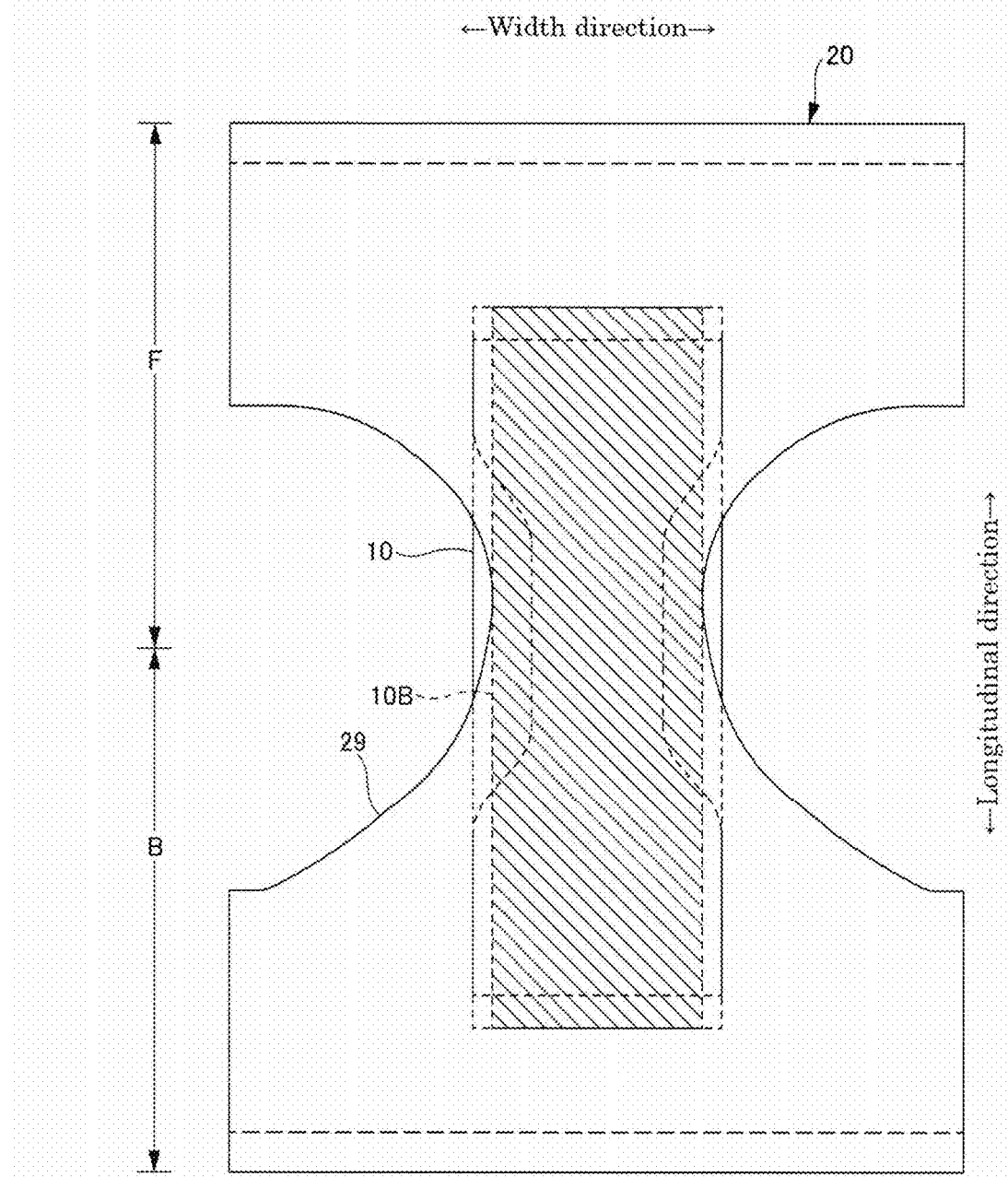
FIG. 7 is a plan view of a main portion of the underpants-type disposable diaper in the completely stretched state.

With reference to FIGS. 4 to 6, the inner member 10 includes a liquid-permeable front face sheet 11 composed of, for example, non-woven fabric, a liquid-impermeable back face sheet 12 composed of, for example, polyethylene, and an absorber 13 between the front face sheet 11 and the back face sheet 12. The inner member 10 is configured to absorb and retain excretory fluid passing through the front face sheet 11. The inner member 10 has typically, but not limited to, a substantially rectangular shape in plan view, as illustrated in the drawings.

The liquid-permeable front face sheet 11, which covers a front face (to come into contact with the skin) of the absorber 13, is preferably composed of perforated or imperforate non-porous non-woven fabric or a porous plastic sheet. Examples of the raw fiber of the non-woven fabric include synthetic fibers, such as olefin fibers e.g., polyethylene fibers and polypropylene fibers, polyester fibers, and polyamide fibers; recycled fibers, such as rayon and cupra; and natural fibers, such as cotton. The non-woven fiber may be prepared by any appropriate process, such as spunlacing, spunbonding, thermal bonding, melt blowing, or needle punching. Among these processes, spunlacing is suitable for achieving sufficient softness and draping, and thermal bonding is suitable for achieving bulkiness and softness. A porous liquid-permeable front face sheet 11 can rapidly absorb urine and is thus superior in dry texture. The liquid-permeable front face sheet 11 extends around the side edges of the absorber 13 to the back face of the absorber 13.

The liquid-impermeable back face sheet 12, which covers the back face (not to come into contact with the skin) of the absorber 13, is composed of a liquid-impermeable plastic sheet, such as a polyethylene sheet or a polypropylene sheet. Recently, the back face sheet 12 with moisture permeability has been preferably used in view of prevention of stuffiness. An example of the liquid-impermeable and moisture-permeable sheet is a microporous plastic sheet produced through melt-kneading an olefin resin, such as a polyethylene resin or a polypropylene resin, and an inorganic filler; forming a sheet with the kneaded materials; and monoaxially or biaxially elongating the sheet.

The absorber 13 may be composed of a well-known basic component, such as an accumulated body of pulp fibers, an assembly of filaments, composed of, for example, cellulose acetate, or non-woven fabric, and the absorber 13 may include as necessary high-absorbent polymer mixed or fixed to the basic component. The absorber 13 may be wrapped with a liquid-permeable and liquid-retainable package sheet 14, such as a crepe sheet, to retain the shape and polymers, as required.

The absorber 13 has a substantially hourglass shape having a narrow portion 13N with a width narrower than those of the front and back end portions of the absorber 13, at a crotch portion. Alternatively, the absorber 13 may have any other shape, for example, a rectangular shape, as appropriate. The size of the narrow portion 13N may be appropriately determined. The narrow portion 13N may have a length of approximately 20 to 50% of the entire length of the diaper along the front-back direction, and a width, at the narrowest region, of approximately 40 to 60% of the entire width of the absorber 13. If the inner member 10 has a substantially rectangular plan view in the case of the absorber with such a narrower part 13N, the inner member 10 has portions free of the absorber 13 according to the narrower part 13N of the absorber 13.

Three-dimensional gathers BS, which are configured to fit around the legs, are formed on two sides of the inner member 10. With reference to FIGS. 5 and 6, the three-dimensional gathers BS are each composed of a gather non-woven fabric 15 folded into a duplicate sheet consisting of a fixed section fixed to the side of the back face of the inner member, a main section extending from the fixed section around a side of the inner member to the side of the front face of the inner member, lying down sections formed by fixing the front end and back end of the main section in a lying down state to the side of the front surface of the inner member, and a free section formed in an un-fixed state between the lying down sections.

Elongated gather elastic members 16 are disposed in the tip portion of the free sections of the duplicate sheet. As illustrated by the chain double-dashed line in FIG. 5, part of the non-woven fabric protruding from a side edge of the absorber is erected by elastic stretching force of the gather elastic members 16 to form a three-dimensional gather BS in a completed product.

The liquid-impermeable back face sheet 12 and the liquid-permeable front face sheet 11 are turned at two sides of the absorber 13 in the width direction toward the back face of the absorber 13. The liquid-impermeable back face sheet 12 is preferably opaque to allow brownish color of urine and feces to be imperceptible. A preferred opaque sheet is a plastic film containing colorant or filler, such as calcium carbonate, titanium oxide, zinc oxide, white carbon, clay, talc, or barium sulfate.

The gather elastic members 16 may be composed of a common elastic material, such as styrene rubber, olefin rubber, urethane rubber, ester rubber, polyurethanes, polyethylene, polystyrene, styrene-butadiene, silicones, or polyesters. The gather elastic members 16 preferably have a fineness of 925 dtex or less, a tension of 150 to 350%, and are preferably disposed at an interval of 7.0 mm or less, in view of invisibility from the external side. The gather elastic members 16 may be shaped in threads, as illustrated in the drawings, or tapes having a certain width.

Like the liquid-permeable front face sheet 11, the gather non-woven fabric 15 may be made of synthetic fibers, such as olefin fibers e.g., polyethylene fibers and polypropylene fibers, polyester fibers, and polyamide fibers; recycled fibers, such as rayon and cupra; and natural fibers, such as cotton, and may be prepared by any appropriate process, such as spunbonding, thermal bonding, melt blowing, or needle punching. In particular, the non-woven fabric 15 preferably has a reduced basis weight and high air-permeability in view of prevention of stuffiness. Furthermore, the gather non-woven fabric 15 is preferably a water-repellent non-woven fabric coated with a water-repellent agent, such as a silicone-based agent, a paraffin-metallic agent, or an alkyl chromic chloride agent, for prevention of permeation of urine and occurrences of diaper rashes, and an enhancement in dry texture to the skin.

<Exemplary Structure of Outer Member>

With reference to FIGS. 4 to 6, the outer member 20 includes a first sheet layer 20A, a second sheet layer 20B, and an elastic film 30 and elongated elastic members 24 that are disposed between the first sheet layer 20A and the second sheet layer 20B. The elongated waist elastic members 24 are disposed along the width direction of the outer member 20, imparting elasticity in the width direction. The entire outer member 20 has a substantially hourglass shape having recessed portions along leg-lines 29 at the two sides and at the middle of the outer member 20 in plan view. The recessed portions along the leg-lines 29 are configured to form leg openings. Alternatively, the outer member 20 may be composed of front and back segments separated from each other at the crotch portion.

In more detail, the outer member 20 illustrated in the drawings includes the waist elastic members 24 in the waist portions 23 in the torso portions T defined as vertical ranges with the side seal portions 21 at which the front body F is to be bonded to the back body B. The elongated waist elastic members 24 are rubber threads disposed at an interval in the longitudinal direction and imparting stretching force to tighten the torso of the body. Three or more, preferably five or more waist elastic members 24 are disposed at an interval of approximately 3 to 8 mm to define predetermined stretchable zones, rather than densely disposed substantially in a bundle. The stretch rate of the waist elastic member 24 may be determined as appropriate, and is approximately 230 to 320% for adults, in usual cases.

The waist elastic members 24 are rubber threads in the embodiments illustrated in the drawings. Alternatively, the waist elastic members 24 may be stretchable tapes, for example. Instead of the waist elastic members 24, an elastic film described below may extend to the waist portions 23. The waist elastic members 24 are held in turn-up sections 20C, which are parts of the second sheet layer 20B turned at the edges of the waist opening toward the internal surface side. Alternatively, the waist elastic members 24 may be held between the first sheet layer 20A and the second sheet layer 20B.

The first sheet layer 20A and the second sheet layer 20B may be any sheet members, preferably non-woven fabrics in view of air permeability and softness. The non-woven fabric may be made of any raw fiber. Examples of the raw fiber include synthetic fibers, such as olefin fibers e.g., polyethylene fibers and polypropylene fibers, polyester fibers, and polyamide fibers; recycled fibers, such as rayon and cupra; natural fibers, such as cotton; and blend or conjugate fibers composed of two or more of these fibers. The non-woven fabric may be prepared through any process. Examples of the preparing process include well-known processes, such as spunlacing, spunbonding, thermal bonding, melt blowing, needle punching, air-through processes, and point bonding. The non-woven fabric preferably has a basis weight of approximately 12 to 20 $g/m^2$. The first sheet layer 20A and the second sheet layer 20B may be composed of paired facing layers prepared by folding a single member.

Figure 2:
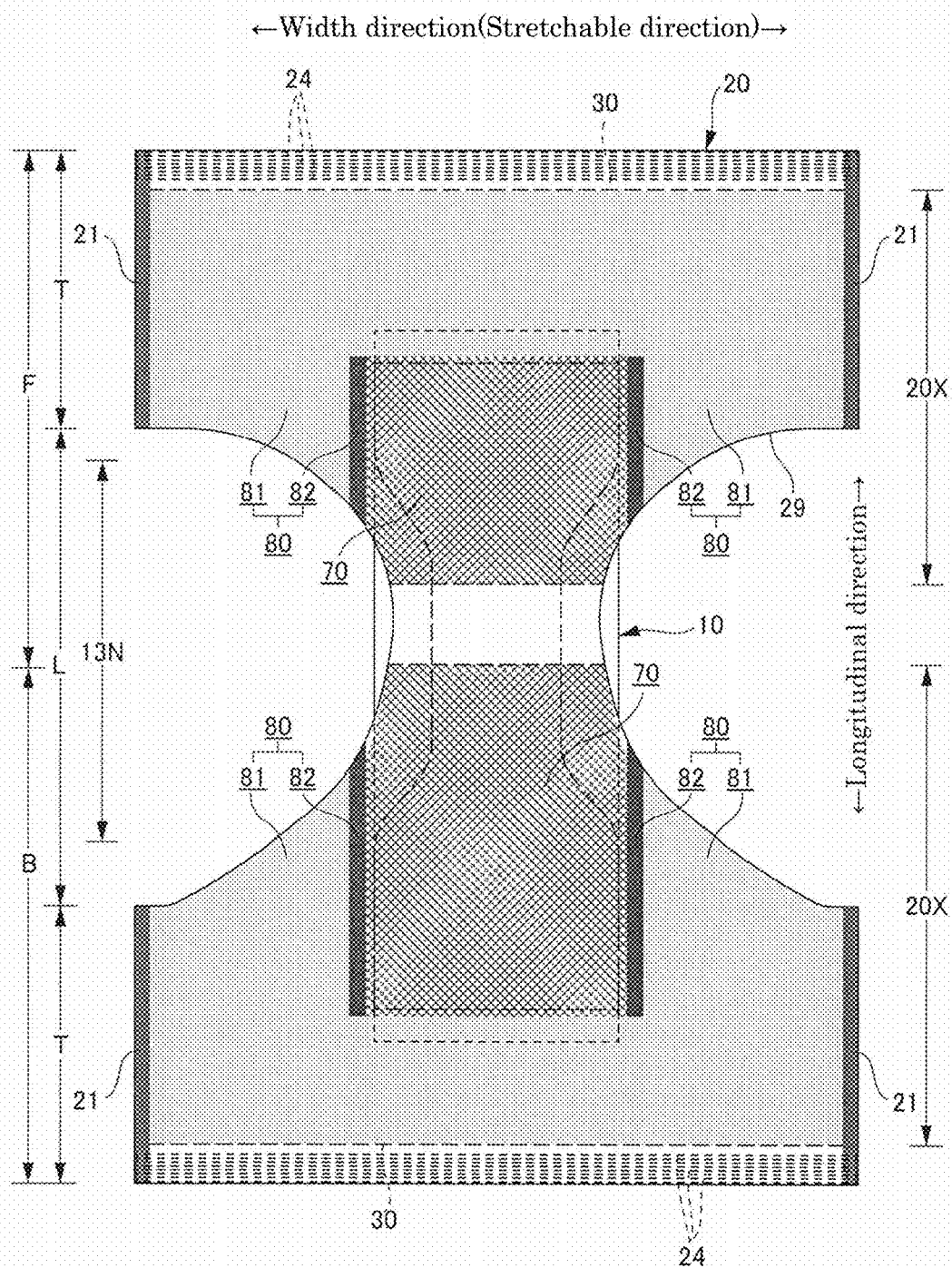
FIG. 2 is a plan view illustrating the external surface side of an underpants-type disposable diaper in the completely stretched state.
Figure 3:
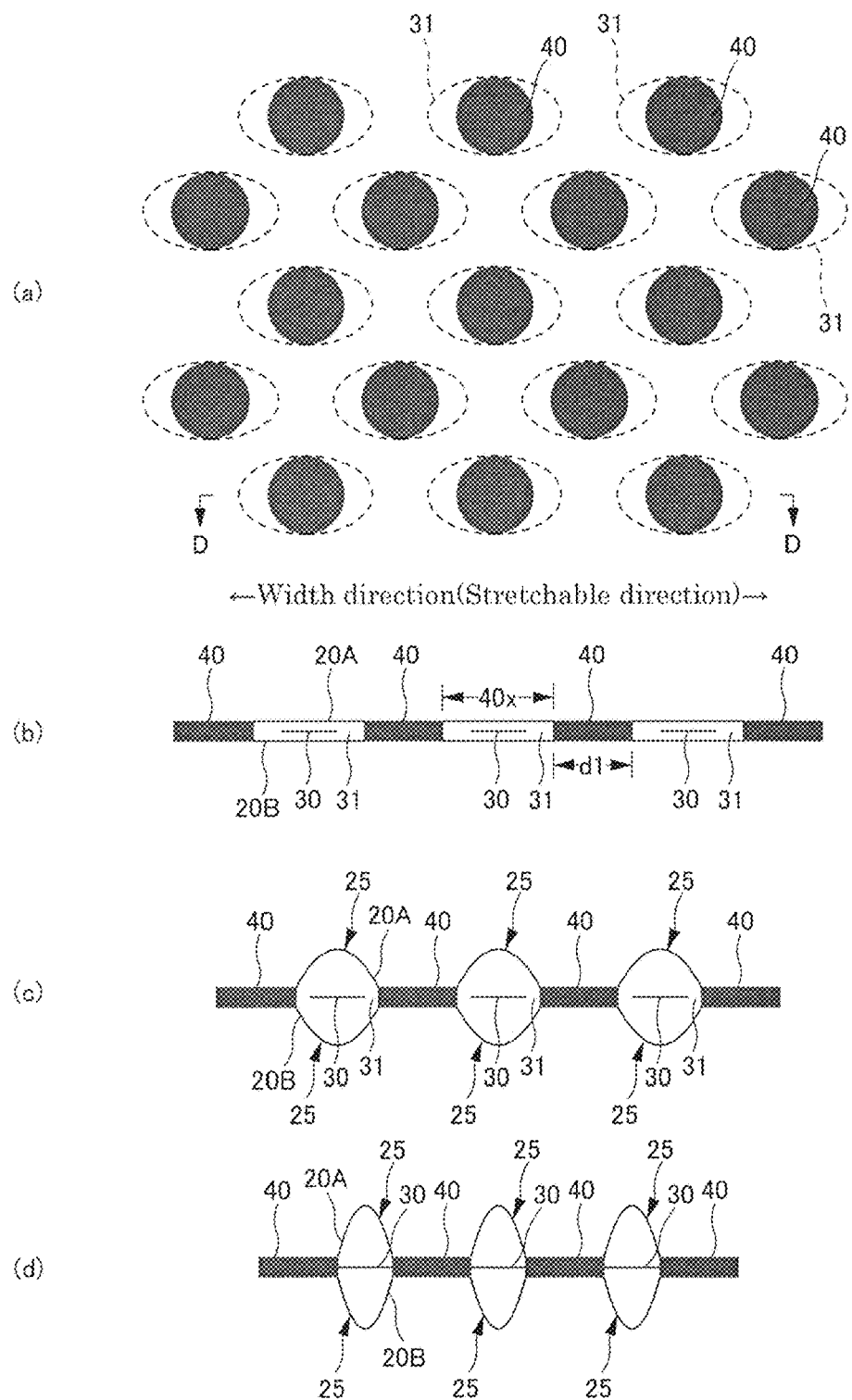
FIG. 3(a) is a plan view of a main portion of the outer member.
FIG. 3(b) is a cross-sectional view of the main portion taken along the line D-D in FIG. 3(a)
FIG. 3(c) is a cross-sectional view of the main portion in a worn state.
FIG. 3(d) is a cross-sectional view of the main portion in the natural-length state.

With reference to FIG. 2, the present invention is characterized by stretchable structures 20X formed in the torso portions T in the front body F and the back body B of the outer member 20, and an intermediate portion L between the two torso portions T. In detail, the stretchable structures 20X of the outer member 20 include non-stretchable regions 70, which are parts of the outer member 20 overlapping with the absorber 13 in an intermediate portion of the outer member 20 in the width direction (the non-stretchable regions 70 may entirely or partly overlap with the absorber 13); and stretchable regions 80 extending from the ends of the non-stretchable regions 70 to the side seal portions 21 at the both sides in the width direction. With reference to FIG. 3, an elastic film 30 is disposed between the first sheet layer 20A and the second sheet layer 20B over the entire stretchable regions 80 and the non-stretchable regions 70. The elastic film 30 is stretched in the width direction and the first sheet layer 20A is bonded to the second sheet layer 20B at a large number of dot-like joints 40 arrayed at an interval in the stretchable direction and the direction perpendicular to the stretchable direction via through holes 31 formed in the elastic film 30.

Basically, as the area rate of the dot-like joints 40 increases in the stretchable structure 20X including such an elastic film 30, portions contracted by the elastic film 30, of the first sheet layer 20A and the second sheet layer 20B decrease, and the elongation at elastic limit is likely to decrease. Accordingly, the area rate of the through holes 31 in the elastic film 30 increases, and thus the proportion of portions of the elastic film 30 continuing in the stretchable direction decreases in a direction perpendicular to the stretchable direction. Accordingly, the contraction force to be generated in a stretched state decreases, and the risk of rupture of the elastic film 30 increases. In view of such characteristics, the area rate of the dot-like joints 40 in the non-stretchable regions 70 is determined to be larger than that in the stretchable regions 80, such that the elongation at elastic limit in the extending direction is 130% or less (preferably 120% or less, more preferably 100%). In contrast, the area rate of the dot-like joints 40 in the stretchable regions 80 is determined to be smaller than that in the non-stretchable regions 70, such that the elongation at elastic limit in the stretchable direction is 200% or higher (preferably 265 to 295%).

When the elastic film 30 is in the natural-length state as illustrated in FIG. 3 (*d*), the first sheet layer 20A and the second sheet layer 20B are raised apart from each other, forming contracted wrinkles 25 extending in a direction intersecting with the stretchable direction in the stretchable region 80. When the elastic film 30 is stretched to an extent in the width direction as illustrated in FIG. 3(*c*), the contracted wrinkles 25 are still remain while being stretched. In addition, as illustrated in the drawings, the first sheet layer 20A and the second sheet layer 20B are not bonded to the elastic film 30 in regions except at least between the first sheet layer 20A and the second sheet layer 20B in the dot-like joints 40; therefore, as apparent from FIG. 3(c) illustrating the worn state and FIGS. 3(a) and 3(b) illustrating a completely stretched state of the first sheet layer 20A and the second sheet layer 20B, gaps are formed between each through hole 31 in the elastic film 30 and the corresponding dot-like joint 40. In the case of the elastic film 30 composed of a nonporous material, these gaps contribute to air permeability. The contracted wrinkles 25 of sample products in the worn state and the natural-length state are also shown in the photographs FIGS. 12 to 14.

Figure 12:
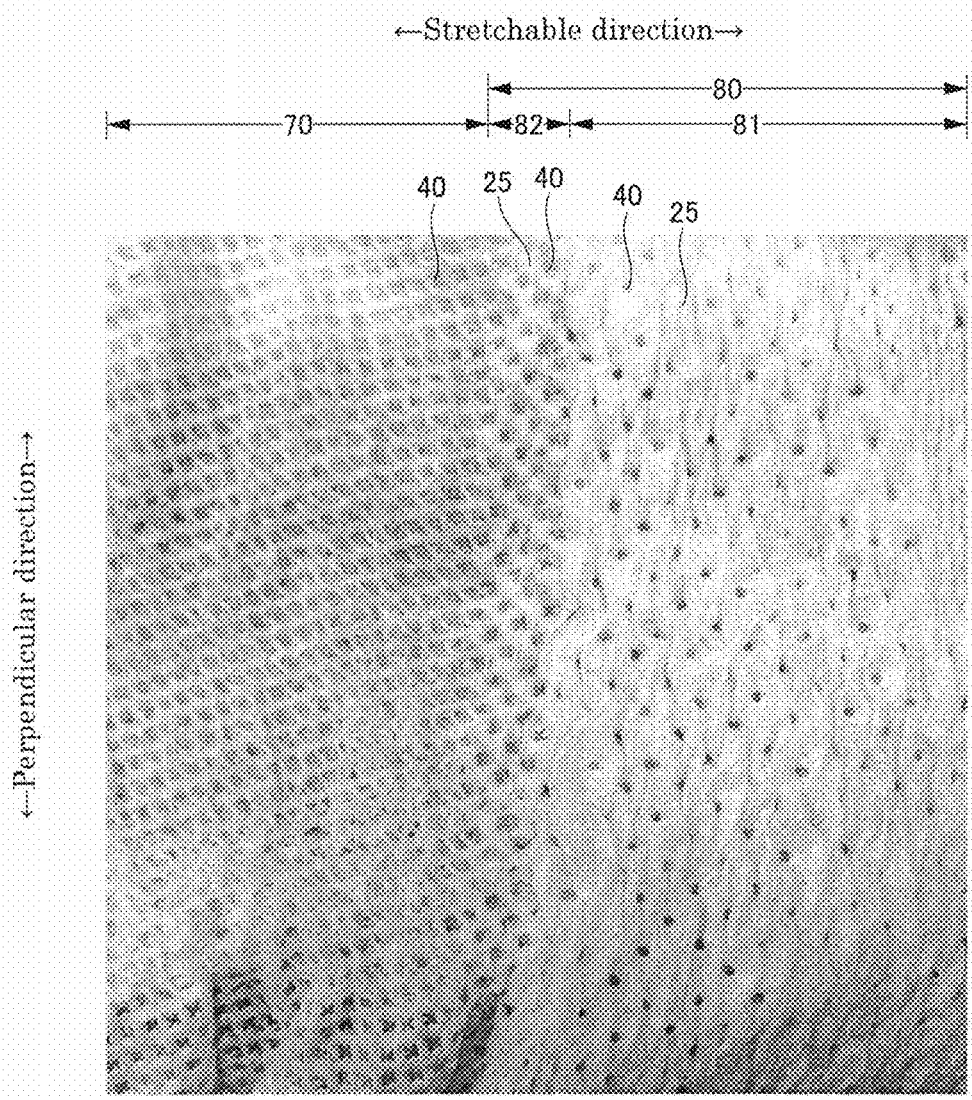
FIG. 12 is a photograph showing a sample in the natural-length state according to an embodiment.
Figure 13:
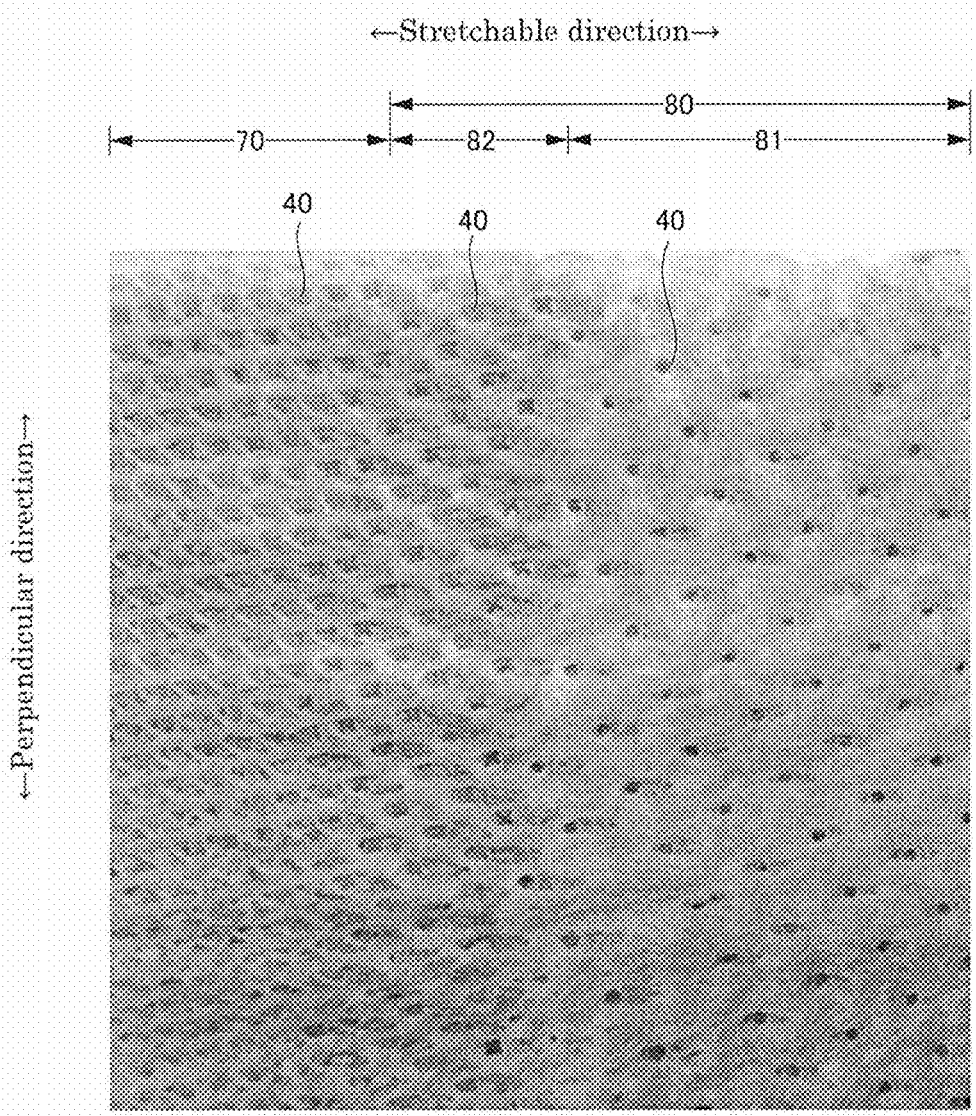
FIG. 13 is a photograph showing a sample in a stretched state according to an embodiment.
Figure 14:
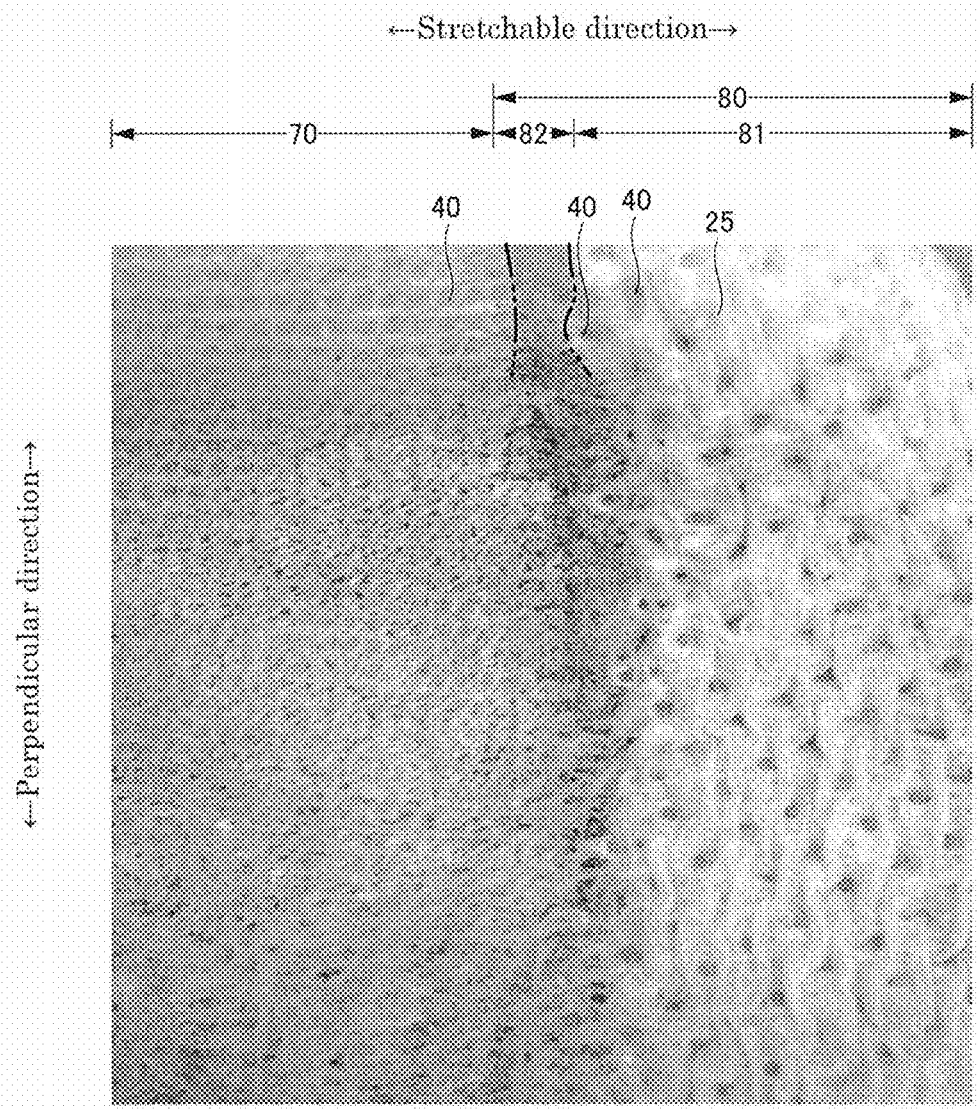
FIG. 14 is a photograph showing a sample in the natural-length state after ruptures of an elastic film.

As apparent from FIGS. 12 to 14, streaks or microwrinkles are formed between the dot-like joints 40 in the non-stretchable region 70; however, the elasticity of the non-stretchable region 70 is substantially eliminated because of a high area rate of the dot-like joints 40.

With reference to FIGS. 2 and 9(a), the stretchable structure is characterized by buffer stretchable sections 82, which are ends of the stretchable regions 80 adjacent to the non-stretchable regions 70. The buffer stretchable sections 82 have a larger area rate of the dot-like joints 40 than that of the remaining sections or main stretchable sections 81 of the stretchable regions 80. When stretched, the buffer stretchable sections 82 are assumed to cause the following variations: In the case where the buffer stretchable sections 82 and the main stretchable sections 81 are stretched from the natural-length state by gradually increasing stress, there are the first phase and the second phase. In the first phase, while both of the buffer stretchable sections 82 and the main stretchable sections 81 are stretched, the buffer stretchable sections 82 are stretched to the elastic limit into a completely stretched state (illustrated in FIG. 3(b)) earlier than the main stretchable sections 81 and the main stretchable sections 81 are in an incompletely stretched state (illustrated in FIG. 3(c)). The main stretchable sections 81 go through the first phase and then the second phase where the main stretchable sections 81 are stretched to the elastic limit into a completely stretched state (illustrated in FIG. 3(b)). In the first phase, the buffer stretchable sections 82 having a low elongation at elastic limit are stretched; therefore, a small tension is applied to boundaries between the buffer stretchable sections 82 and the non-stretchable regions 70 of the elastic film 30. Ruptures of the elastic film 30 at the boundaries between the buffer stretchable sections 82 and the non-stretchable regions 70 are thereby prevented. In the second phase, until the main stretchable sections are in a completely stretched state, tension corresponding to the elongation of the main stretchable sections 81 is applied to the main stretchable sections 81, the buffer stretchable sections 82, and the non-stretchable regions 70; however, since the buffer stretchable sections 82 cannot be stretched any more after the first phase, and tension applied to the non-stretchable regions 70 and the buffer stretchable sections 82 is entirely supported by the first sheet layer 20A and the second sheet layer 20B. As a result, the tension applied to the boundaries between the buffer stretchable sections 82 and the non-stretchable regions 70 of the elastic film 30 does not exceed the elongation at elastic limit in the first phase. Ruptures of the elastic film 30 along the boundaries between the buffer stretchable sections 82 and the non-stretchable regions 70 are thereby prevented, as in the first phase.

In contrast, if buffer stretchable sections 82 are not provided as illustrated in FIG. 9(b), the stretchable region 80 has a high elongation at elastic limit, and tension applied to the boundary between the stretchable region 80 and the non-stretchable region 70 of the elastic film 30 increases until the boundary between the stretchable region 80 and the non-stretchable region 70 of the elastic film 30 is stretched to the elongation at elastic limit into a completely stretched state. The elastic film 30 is thereby likely to rupture along the boundary between the stretchable region 80 and the non-stretchable region 70 (the edges of the ruptured elastic film is indicated by the chain double-dashed lines), as illustrated in FIG. 14.

In view of the principle described above, it is preferred that the elongation at elastic limit of the buffer stretchable section 82 be smaller than a tensile elongation in the stretchable direction of the elastic film 30 having a width equal to an interval between two adjacent through holes 31 formed in the elastic film 30 and arrayed in the direction perpendicular to the stretchable direction and in the non-stretchable region 70, to certainly prevent the rupture of the elastic film 30 at the boundary between the stretchable region 80 and the non-stretchable region 70.

Each of the dot-like joints 40 and through holes 31 may have any shape, for example, circular, oval, polygonal (for example, triangular), astral, or cloud shape, in the natural-length state. The size of each dot-like joint 40 may be appropriately determined. At an excessively large size, the hardness of the joints 40 significantly affects the touch, whereas at an excessively small size, the bonded area is too small to certainly bond the layers. Each of the dot-like joints 40 preferably has an area of approximately 0.14 to 3.5 mm$^2$, in usual cases. Each of the through holes 31 should have an opening area larger than that of the corresponding dot-like joint 40 such that the dot-like joint 40 is formed within the through hole 31. The through hole 31 preferably has an opening area of approximately 1 to 1.5 times the area of the dot-like joint 40.

In general, the preferred areas or area rate of the dot-like joints 40 in each field are as follows.

<Non-Stretchable Region 70>

Area of dot-like joint 40: 0.14 to 3.5 mm$^2$ (in particular, 0.25 to 1.0 mm$^2$)

Area rate of dot-like joints 40: 16 to 45% (in particular, 25 to 45%)

<Main Stretchable Section 81>

Area of dot-like joint 40: 0.14 to 3.5 mm$^2$ (in particular, 0.14 to 1.0 mm$^2$)

Area rate of dot-like joints 40: 1.8 to 19.1% (in particular, 1.8 to 10.6%)

<Buffer Stretchable Section 82>

Area of dot-like joint 40: 0.14 to 3.5 mm$^2$ (in particular, 0.25 to 1.0 mm$^2$)

Area rate of dot-like joints 40: 8 to 22.5% (in particular, 12.5 to 22.5%)

Figure 10:
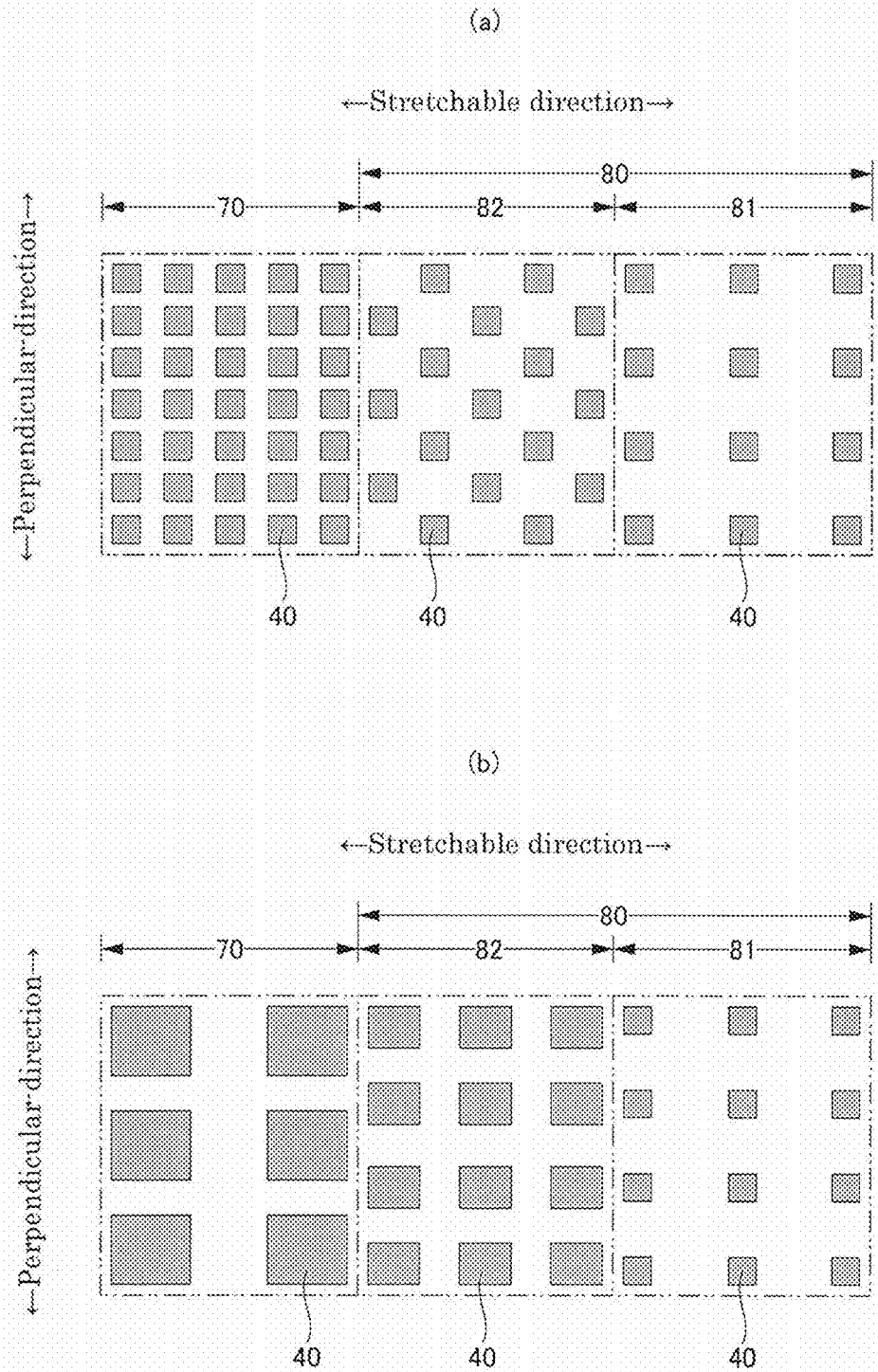
FIG. 10(a) is an enlarged plan view of the main portion illustrating the pattern of dot-like joints in one embodiment.
FIG. 10(b) is an enlarged plan view of the main portion illustrating the pattern of dot-like joints in another embodiment.

To produce three fields (i.e., the non-stretchable region 70, the main stretchable section 81, and the buffer stretchable section 82) having different area rates, the number of the dot-like joints 40 per unit area may be varied, as illustrated in FIG. 10(a), or the area of each dot-like joint 40 may be varied, as illustrated in FIG. 10(b). In the former case, the areas of the dot-like joints 40 may be the same between two or more fields of the non-stretchable region 70, the main stretchable section 81, and the buffer stretchable section 82, or may be different among all the fields. In the latter case, the number of the dot-like joints 40 per unit area may the same between two or more fields of the non-stretchable region 70, the main stretchable section 81, and the buffer stretchable section 82, or may be different among all the fields.

The planar geometries of dot-like joints 40 and the through holes 31 may be appropriately determined. Preferred is regularly repeated geometry, such as rhombic lattice or hexagonal lattice (also referred to as staggered lattice), square lattice, rectangular lattice, or parallelotope lattice (where a group of diagonally parallel arrays intersects another group of diagonal parallel arrays, as shown in the drawings). Alternatively, the joints 40 may be arrayed in regularly repeated groups (the geometry of each group may be regular or irregular, in other words, may be in a pattern or characteristic letters, for example). The geometries of the joints 40 and the through holes 31 may be the same or different among the main stretchable section 81, the buffer stretchable section 82, and the non-stretchable region 70.

The elastic film 30 may be composed of any resin film having elasticity. The elastic film 30 may have no pore or may have a large number of pores or slits for air permeability. In a preferred embodiment, the elastic film 30 has a tensile strength in the stretchable direction in the range of 8 to 25 N/35 mm, a tensile strength in the direction perpendicular to the stretchable direction in the range of 5 to 20 N/35 mm, a tensile elongation in the stretchable direction in the range of 450 to 1050%, and a tensile elongation in the direction perpendicular to the stretchable direction in the range of 450 to 1400%. The tensile strength and the tensile elongation at break are measured at an initial chuck interval of 50 mm and a speed of testing of 300 mm/min with a tensile tester (for example, AOUTGRAPHAGS-G100N available from SHIMADZU) in accordance with JIS K7127: 1999 "Plastics—Determination of tensile properties", except that the test piece is a rectangle with a width of 35 mm and a length of 80 mm. The elastic film 30 may have any thickness, preferably in the range of approximately 20 to 40 μm.

Figure 8:
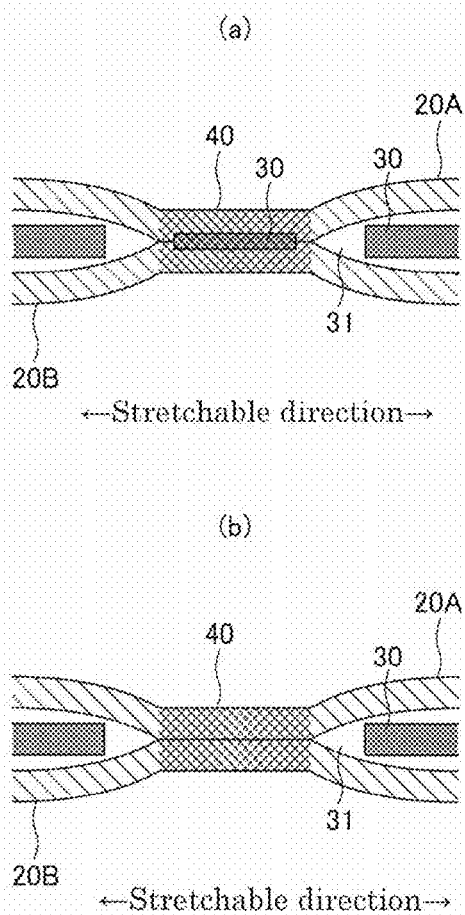
FIG. 8(a) is a schematic cross-sectional view of the main portion of the outer member in a state stretched to some extent in the width direction in one embodiment.
FIG. 8(b) is a schematic cross-sectional view of the main portion of the outer member in a state stretched to some extent in the width direction in another embodiment.

The first sheet layer 20A and the second sheet layer 20B are bonded to each other directly or through the elastic film 30 or any other sheet at the dot-like joints 40. FIGS. 8(*a*) and 8(*b*) illustrate two representative examples of a bonding structure. As in the embodiment illustrated in FIG. 3, the first sheet layer 20A and the second sheet layer 20B are bonded to each other via the through holes 31 formed in the elastic film 30, and are separate from the elastic film 30 at portions except at least between the first sheet layer 20A and the second sheet layer 20B in the dot-like joints 40 (portions in a diagonal-lattice pattern in FIG. 8) in the bonding structures illustrated in FIGS. 8(*a*) and 8(*b*). The bonding structures may be produced by forming the dot-like joints 40 with the sequence pattern of raised ridges of the patterned calender rolls disclosed in Japanese Unexamined Patent Application Publication (Translation of PCT Application No. 2004-532758). It seems that the method disclosed in Japanese Unexamined Patent Application Publication (Translation of PCT Application No. 2004-532758), however, extrudes the elastic film 30 without melting of the elastic film 30. In this case, any fraction of the elastic film 30 does not remain between the first sheet layer 20A and the second sheet layer 20B, as illustrated in FIG. 8(*b*), and movable fractions (not shown) of the elastic film 30 may remain around through hole 31. To address the problem, the material and processing parameters, such as processing temperature, of the elastic film 30 may be appropriately determined in the method disclosed in Japanese Unexamined Patent Application Publication (Translation of PCT Application No. 2004-532758) so that the elastic film 30 is melted. A fraction of the elastic film 30 thereby remain in each of the dot-like joint 40 after melting of the elastic film 30, as illustrated in FIG. 8(*a*). The bonding structure in which fractions of the melted elastic film 30 remain between the first sheet layer 20A and the second sheet layer 20B at the dot-like joint 40 can be referred to as the bonding structure in which the first sheet layer 20A and the second sheet layer 20B are bonded to the elastic film 30 at the dot-like joints 40. In other words, in the bonding structure, parts of the first sheet layer 20A and the second sheet layer 20B outside at least between the first sheet layer 20A and the second sheet layer 20B in the dot-like joints 40 are separated from the elastic film 30 (this does not include that the parts of the first sheet layer 20A and the second sheet layer 20B are bonded to surrounding parts of the elastic film 30 (i.e., edge of the through holes 31) at the dot-like joints 40). In this case, the area of each of the dot-like joints 40 is substantially equal to the area of the corresponding through hole.

In the embodiments illustrated in the drawings, the stretchable structures 20X of the present invention are applied to portions of the outer member 20 except the waist portions. In another embodiment, the stretchable structures 20X may be applied to portions of the outer member 20 including the waist portions. In still another embodiment, an intermediate portion L between the torso portion T of the front body F and the torso portion T of the back body B may be free from the stretchable structure 20X. Besides the underpants-type disposable diapers, the stretchable structure 20X is applicable to stretchable regions, such as torso portions and fastening tapes of tape-type disposable diapers, and plane and three-dimensional gathers widely used in a variety of absorbent articles.

Figure 11:
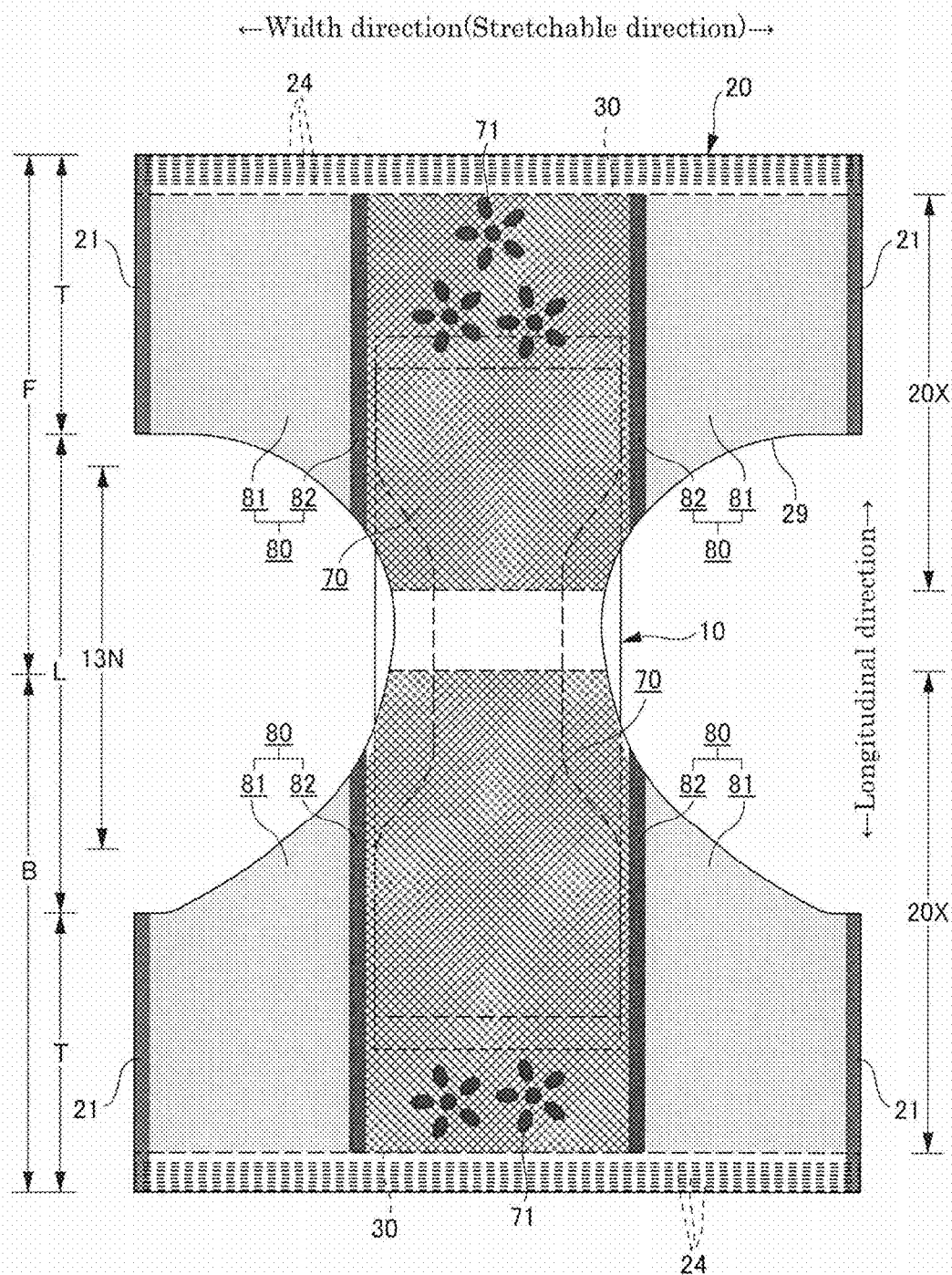
FIG. 11 is a plan view illustrating the external surface side of the underpants-type disposable diaper in the completely stretched state.

In another embodiment illustrated in FIG. 11, the non-stretchable regions 70 in the form of marks 71 consisting of the dot-like joints 40 are disposed in portions outside the region overlapping with the absorber 13. Also in this case, buffer stretchable sections may be formed between the non-stretchable regions 70 and the stretchable regions 80. Examples of the marks 71 include common marks that are well-known in the field of absorbent articles, for example, decorative patterns, such as small illustrations and characters, functional indicators indicating usage instructions, usage guides, and sizes, and marks indicating manufacturers, product names, and distinctive functions. Although the marks 71 are in the form of plant (flower) patterns in the embodiment illustrated in FIG. 12, it should be understood that the marks 71 may be formed in any pattern, such as abstract patterns, animal patterns, and phenomenal patterns.

<Front and Back Cover Sheets>

With reference to FIGS. 1 and 4, front and back cover sheets 50, 60 may be provided to cover the front and back end portions of the inner member 10 attached to the internal face of the outer member 20 to prevent leakage from the front and rear edges of the inner member 10. In more detail, the front cover sheet 50 extends over the entire width of the front body F on the internal face of the front body F from the internal face of the turn-up section 20C at the waist-side end of the front body F to a position overlapping with the front end portion of the inner member 10. The back cover sheet 60 extends on the internal face of the back body B over the entire width, and extends over the entire width of the back body B from the internal face of the turn-up section 20C at the waist-side end of the back body B to a position overlapping with the back end portion of the inner member 10, in the embodiment illustrated in the drawings. Minor non-bonded regions are provided over the entire width (or only at the central portion) at side edge portions of the front and back cover sheets 50 and 60 at the crotch portion-side. The front and back cover sheets 50 and 60 having such non-bonded regions can prevent leakage of the adhesive and function as barriers against leakage when slightly suspended from the front face sheet.

The front and back cover sheets 50, 60 as separate components in the embodiment illustrated in the drawings advantageously enlarge the range of choice of material, but disadvantageously needs additional materials and manufacturing processes. To address the disadvantage, in another embodiment, the turn-up sections 20C formed by turning up the outer member 20 toward the internal surface side of the diaper are respectively extended to portions overlapping with the inner member 10, so as to have the same function as that of the front and back cover sheets 50, 60.

<Terminology in Specification>

The terms used in the specification have the following meanings unless otherwise stated.

"Stretch rate" represents a value relative to the natural length (100%).

"Basis weight" is determined as follows: After the sample or test piece is preliminarily dried, it is allowed to stand in a testing chamber or machine under the standard condition (temperature: 20±5° C., relative humidity: 65% or less) until the constant mass. The preliminary drying represents that the sample or test piece reaches constant mass in an environment within a relative humidity of 10 to 25% and at a temperature not exceeding 50° C. The fiber of an official regain of 0.0% does not need preliminary drying. A cut sample with a size of 200 mm by 250 mm (±2 mm) is prepared from the test piece at the constant mass with a cutting template (200 mm by 250 mm, ±2 mm). The sample is weighed and the weight is multiplied by 20 into the weight per square meter. The resulting value is defined as basis weight.

"Thickness" is automatically determined with an automatic thickness gauge (KES-G5 handy compression measurement program) under the conditions of a load of 10 gf/cm$^2$ and a pressurization area of 2 cm$^2$.

INDUSTRIAL APPLICABILITY

The present invention is applicable to underpants-type disposable diapers as described above, and is also applicable to a variety of absorbent articles having stretchable structures, such as tape-type and pad-type disposable diapers and sanitary napkins.

REFERENCE NUMERALS

B: back body, F: front body, T: torso portion, L: intermediate portion, 10: inner member, 11: liquid permeable front face sheet, 12: liquid impermeable back face sheet, 13: absorber, 13N: narrow portion, 14: package sheet, 15: gather nonwoven fabric, 16: gather elastic member, 20: outer member, 20A: first sheet layer, 20B: second sheet layer, 20C: turn-up section, 20X: stretchable structure, 21: side seal portion, 24: waist elastic member, 25: contracted wrinkle, 29: leg line, 30: elastic film, 31: through hole, 40: dot-like joint, 70: non-stretchable region, 71: mark, 80: stretchable region, 81: main stretchable section, 82: buffer stretchable section

The invention claimed is:

1. A stretchable structure of an absorbent article comprising:
   a stretchable region stretchable in a stretchable direction; and
   a non-stretchable region continuing from the stretchable region, wherein
   a laminate comprising a first sheet layer, a second sheet layer, and an elastic film disposed between the first sheet layer and the second sheet layer extends over the stretchable region and the non-stretchable region,
   the first sheet layer and the second sheet layer are bonded to each other at a large number of dot-like joints via through holes formed in the elastic film stretched along surfaces of the first sheet layer and the second sheet layer in the stretchable direction, the dot-like joints being arrayed at intervals in the stretchable direction and a direction perpendicular to the stretchable direction, wherein the stretchable region comprises the dot-like joints,
   an area rate of the dot-like joints in the non-stretchable region is larger than an area rate of the dot-like joints in the stretchable region, and the non-stretchable region has an elongation at elastic limit of 130% or less in the stretchable direction,
   the area rate of the dot-like joints in the stretchable region is smaller than the area rate of the dot-like joints in the non-stretchable region, and the stretchable region has an elongation at elastic limit of 200% or larger,
   an end of the stretchable region adjacent to the non-stretchable region is a buffer stretchable section, an area rate of the dot-like joints in the buffer stretchable section being larger than an area rate of the dot-like joints in a main stretchable section not including the buffer stretchable section,
   where the buffer stretchable section is configured to have an elongation at elastic limit smaller than a tensile elongation at a break in the stretchable direction of the elastic film having a width equal to an interval between two adjacent through holes formed in the elastic film in the non-stretchable region and arrayed in the direction perpendicular to the stretchable direction,
   wherein the buffer stretchable section prevents rupture of the elastic film at a boundary between the stretchable region and the non-stretchable region.

2. The stretchable structure of the absorbent article according to claim 1,
   wherein
   the dot-like joints are formed by welding materials of the first sheet layer and the second sheet layer, and
   at least edges of the through holes formed in the elastic film are cured.

3. The stretchable structure of the absorbent article according to claim 1, wherein
   each of the dot-like joints has an area of 0.14 to 3.5 mm$^2$,
   each of the through holes has an area that is 1 to 1.5 times the area of each of the dot-like joints,
   the area rate of the dot-like joints is 16 to 45% in the non-stretchable region,
   the area rate of the dot-like joints is 1.8 to 19.1% in the main stretchable section,
   the area rate of the dot-like joints is 8 to 22.5% in the buffer stretchable section.

4. The stretchable structure of the absorbent article according to claim 1, wherein
   the elastic film has a tensile strength of 8 to 25 N/35 mm in the stretchable direction, a tensile strength of 5 to 20 N/35 mm in the direction perpendicular to the stretchable direction, a tensile elongation of 450 to 1050% in the stretchable direction, and a tensile elongation of 450 to 1400% in the direction perpendicular to the stretchable direction.

5. An underpants-type disposable diaper comprising:
   an outer member comprising a front body and a back body; and
   an inner member comprising an absorber, the inner member being fixed to an internal face of the outer member, wherein two side edges of the front body of the outer member are respectively bonded to two side edges of the back body of the outer member to define side seal portions, and an annular torso, a waist opening, and paired leg openings are thereby formed, the outer member has the stretchable structure of the absorbent article according to claim 1 such that the stretchable structure is stretchable along a width direction, and the non-stretchable region is a part of the outer member overlapping with the absorber, and the stretchable regions continue from two sides of the non-stretchable region in the width direction.

\* \* \* \* \*